United States Patent
Lentini et al.

(10) Patent No.: US 8,465,208 B2
(45) Date of Patent: Jun. 18, 2013

(54) RE-LUBEABLE CENTER SUPPORT ASSEMBLY FOR BEARING

(75) Inventors: Anthony G. Lentini, St. Clair Shores, MI (US); Robert J. Ostrander, Orchard Lake, MI (US); Christopher J. Steele, Lake Orion, MI (US)

(73) Assignee: ArvinMeritor Technology, LLC, Troy, MI (US)

( * ) Notice: Subject to any disclaimer, the term of this patent is extended or adjusted under 35 U.S.C. 154(b) by 591 days.

(21) Appl. No.: 12/731,198

(22) Filed: Mar. 25, 2010

(65) Prior Publication Data

US 2011/0235954 A1  Sep. 29, 2011

(51) Int. Cl.
*F16C 19/00* (2006.01)
*F16C 27/00* (2006.01)

(52) U.S. Cl.
USPC .......................................... 384/474; 384/535

(58) Field of Classification Search
USPC .................. 384/462, 473, 474, 482, 533, 535, 384/536, 581, 582
See application file for complete search history.

(56) References Cited

U.S. PATENT DOCUMENTS

| | | | | | |
|---|---|---|---|---|---|
| 2,618,520 | A | * | 11/1952 | Anderson et al. | 384/536 |
| 2,826,464 | A | * | 3/1958 | Hawk, Sr. et al. | 384/536 |
| 3,989,323 | A | * | 11/1976 | Lambert | 384/434 |
| 4,274,298 | A | | 6/1981 | Ostrander | |
| 4,463,993 | A | | 8/1984 | Brissette et al. | |
| 4,542,996 | A | | 9/1985 | Brissette et al. | |
| 5,492,418 | A | * | 2/1996 | Brossard | 384/536 |
| 6,379,048 | B1 | | 4/2002 | Brissette | |
| 7,097,363 | B2 | | 8/2006 | Ostrander et al. | |
| 7,779,725 | B2 | | 8/2010 | Eschenburg | |
| 2004/0022467 | A1 | * | 2/2004 | Robb et al. | 384/536 |
| 2007/0060397 | A1 | | 3/2007 | Ostrander et al. | |
| 2010/0046867 | A1 | * | 2/2010 | Hosmer et al. | 384/276 |

* cited by examiner

*Primary Examiner* — James Pilkington
(74) *Attorney, Agent, or Firm* — Brooks Kushman P.C.

(57) ABSTRACT

A center support assembly includes a bearing that supports a driveshaft for rotation about an axis. A shield is fixed to the bearing and a seal is positioned between the shield and the bearing. The shield and seal cooperate to retain lube within the bearing and prevent external contaminants from entering the bearing. A lube passage is formed between an outer surface of the bearing and an inner surface of the shield. At least one externally accessible fitting is in fluid communication with the lube passage and is used to supply additional lubricant to the bearing when needed.

17 Claims, 4 Drawing Sheets

FIG.6

RE-LUBEABLE CENTER SUPPORT ASSEMBLY FOR BEARING

TECHNICAL FIELD

This invention generally relates to a center support assembly for a vehicle driveline.

BACKGROUND

Vehicle drivelines typically include a driveshaft that extends a relatively long distance along a longitudinal length of a vehicle. The driveshaft is usually composed of multiple shafts that are coupled together, and which are supported at spaced locations along a vehicle frame. A center support assembly supports the driveshaft for rotation about a driveshaft axis at one of the spaced locations.

The center support assembly includes a roller bearing that provides structural support for the driveline while accommodating high speed rotation of the driveshaft. The support assembly includes a resilient cushion that is received around the roller bearing, and which is supported within a bracket that secures the center support assembly to the frame. In order to operate effectively, the roller bearing requires a sufficient amount of lubrication and should be protected from environmental contaminants such as water, dust, debris, etc.

In one example, a permanently sealed bearing is used to provide lubricant retention and contaminant exclusion. Such a configuration is not sufficiently effective from service life expectations in severe applications such as when the bearing is operating while being immersed in water or mud.

SUMMARY

A self-aligning bearing can be re-supplied with lubricant by forming a lube passage between the bearing and a shield attached to the bearing. The lubricant is supplied via at least one externally accessible fitting to the lube passage which directs the lubricant to the bearing.

In one example, a center support assembly for the bearing supports a driveshaft for rotation about an axis. The shield is mounted to the bearing and a seal is positioned between the shield and the bearing. The lube passage is formed between an inner surface of the shield and an outer surface of the bearing. At least one fitting is in fluid communication with the lube passage and is externally accessible to supply lubricant to the bearing as needed.

In one example, at least one fitting comprises a plurality of fittings that are in fluid communication with the lube passage.

In one example, a resilient cushion supports the bearing within a bracket. The bracket mounts the bearing to a vehicle structure. In one configuration, the fitting extends through both the bracket and the resilient cushion. In another configuration, the fitting only extends through the bracket.

In one example, the bearing has a fore side and an aft side and the shield includes first and second shield members with the first shield member being attached to the bearing at the fore side and the second shield member being attached to the bearing at the aft side. The lube passage includes a first passage formed between the first shield member and the bearing and a second passage formed between the second shield member and the bearing. The fitting supplies lubricant to both the first and second passages.

These and other features of the present invention can be best understood from the following specification and drawings, the following of which is a brief description.

DETAILED DESCRIPTION

Figure 1:
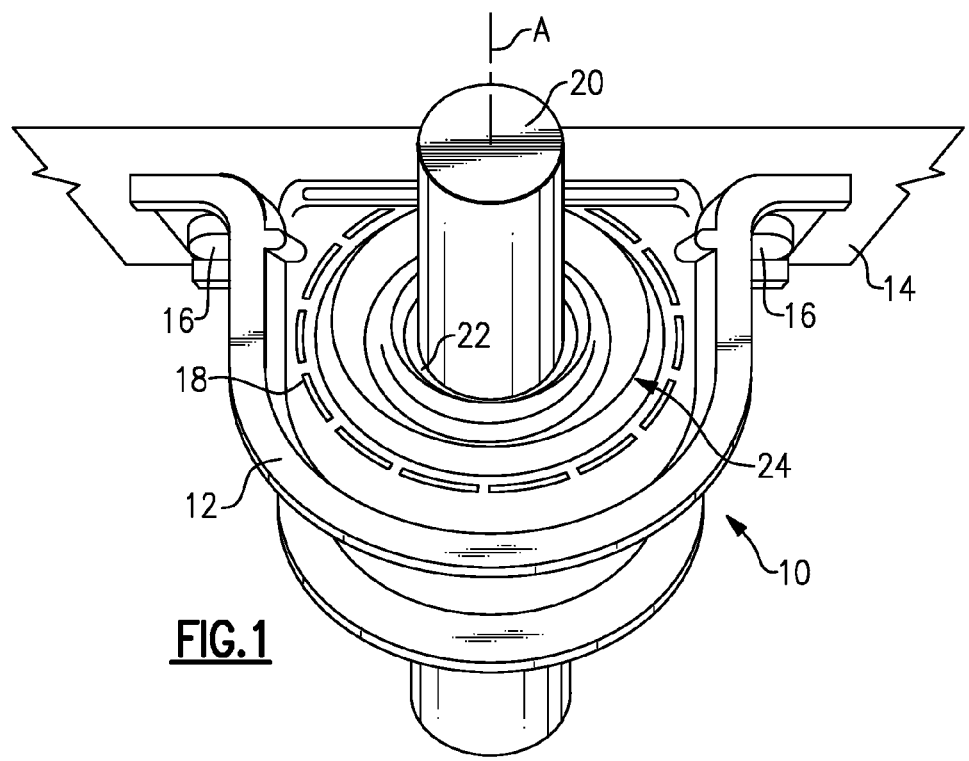
FIG. 1 is a perspective view showing a driveshaft supported within a center support assembly with a self-aligning bearing.

FIG. 1 shows a center support assembly 10 that includes a bracket 12 that is adapted to be attached to a vehicle structure 14, such as a frame rail or frame bracket for example, with fasteners 16. The bracket 12 retains a resilient cushion 18. A driveshaft 20 is supported within a bearing 22 for rotation about an axis A. The bearing 22 is mounted within the cushion 18 such that angular movement of the driveshaft 20 that varies off of being centered along axis A is accommodated by the resiliency of the cushion 18. A protective assembly 24 is mounted over each side of the bearing 22 to protect the bearing 22 from external environmental contaminants.

For further explanation of one example of a self-aligning bearing attention is directed to U.S. Pat. No. 6,379,048 which is assigned to the assignee of the present invention and which is hereby incorporated by reference in its entirety.

Figure 2:
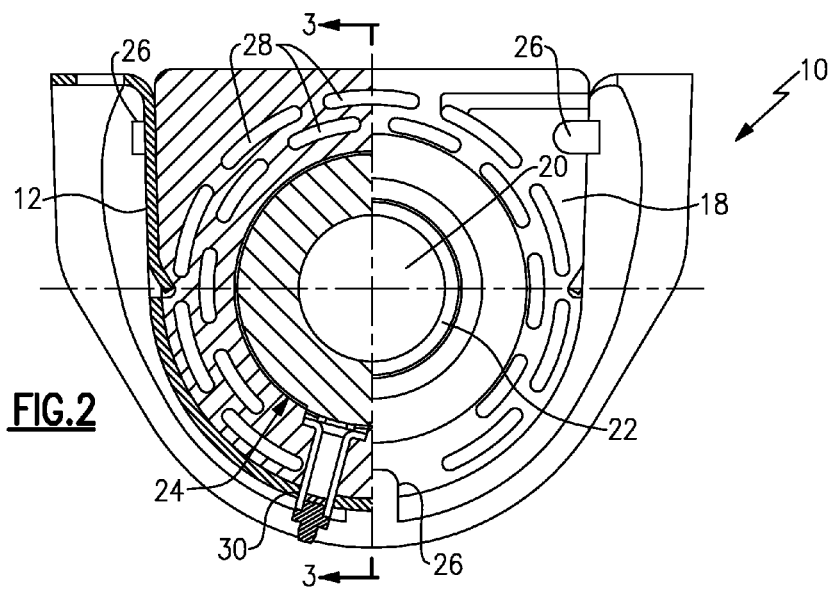
FIG. 2 is a front cross-sectional view of the center support assembly.

As shown in FIG. 2, the bracket 12 includes tabs 26 that are used to hold the cushion 18 in place. The cushion 18 includes a plurality of openings 28 to further enhance resiliency; however, the cushion 18 could also comprise a resilient solid structure. A fitting 30 extends through the bracket 12 and the cushion 18 to interface with the protective assembly 24. The fitting 30 is accessible from an external location to add lubricant to the bearing 22 as needed. This will be discussed in greater detail below.

Figure 3:
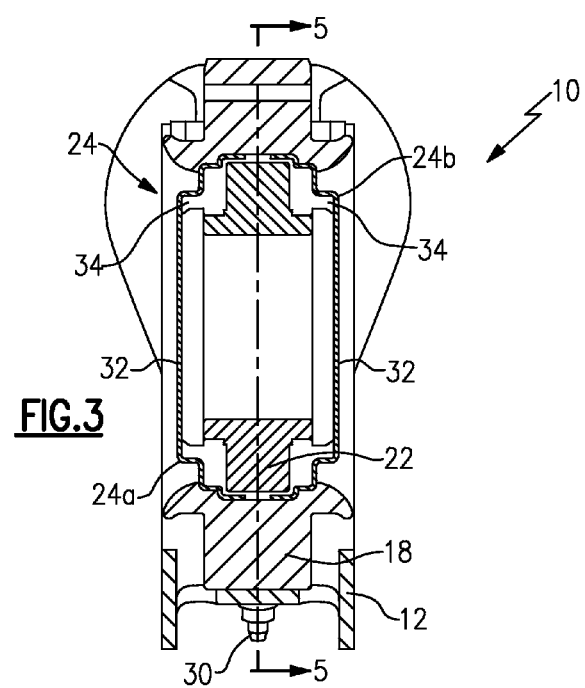
FIG. 3 is a section view taken along lines 3-3 of FIG. 2.

FIG. 3 shows a vertical section taken along lines 3-3 as indicated in FIG. 2. The protective assembly 24 includes a first assembly 24a that is attached to a fore side of the bearing 22 and a second assembly 24b that is attached to an aft side of the bearing 22. These assemblies are sometimes referred to as "clamshells." Further, references to "fore" indicate a direction that is toward a front of a vehicle and references to "aft" indicate a direction that is toward a rear of the vehicle. The first 24a and second 24b assemblies each include a seal 34 that is positioned between a respective shield 32 and the bearing 22. The cushion 18 surrounds and extends circumferentially around the outer surfaces of the protective assembly 24 and bearing 22. The bearing 22 is shown schematically in FIG. 3.

Figure 4:
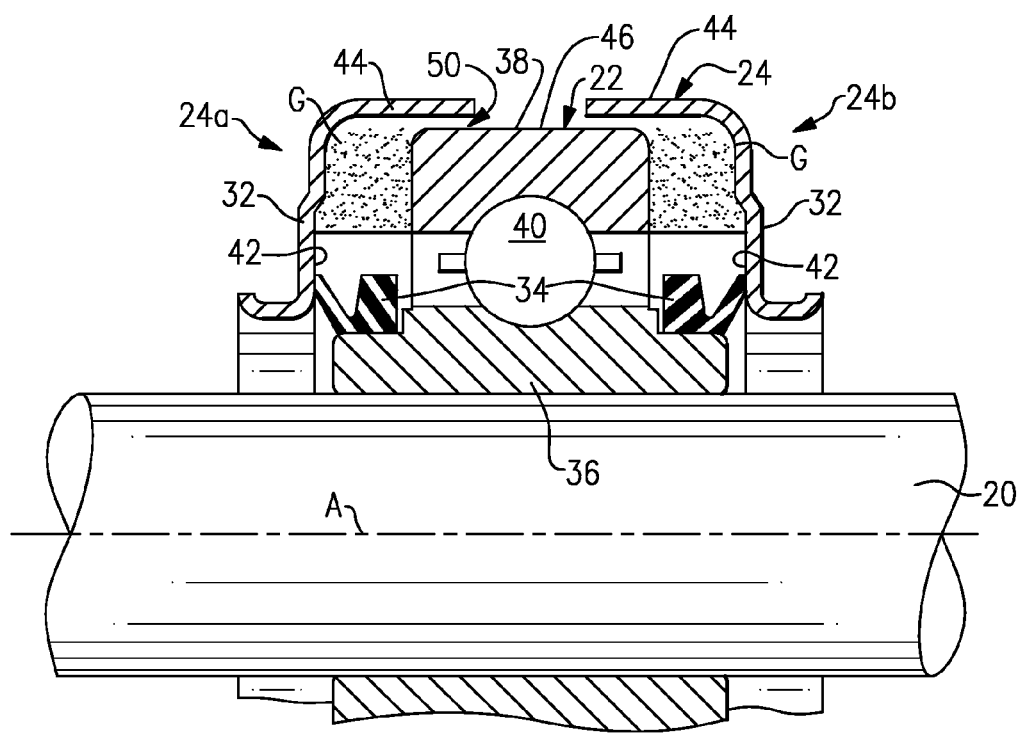
FIG. 4 is a partial cross-sectional view of an upper portion of the center support assembly.

FIG. 4 shows the protective assembly 24 and bearing 22 in greater detail. In the example shown, the bearing 22 comprises a roller bearing having an inner race 36 fixed for rotation with the driveshaft 20 and an outer race 38 that is fixed to the shield 32. Roller elements 40 are supported between the inner 36 and outer 38 races as known.

The shield 32 includes a first portion 42 that extends in a radial direction inward toward the axis A and a second portion 44 that extends in an axial direction over an outer surface 46 of the outer race 38. The seal 34 maintains sealing contact with the inner race 36 and an inner surface of the first portion 42 of the shield 32. The seal 34 can have various configurations and can be attached to either the shield 32 or the bearing 22. For further explanation of a seal as used in the self-aligning bearing attention is directed to U.S. Pat. No. 7,097,363 which is assigned to the assignee of the present invention and which is hereby incorporated by reference in its entirety.

In one example, the shield 32 is a metal stamping that is pressed onto the outer surface 46 of the outer race 38. This outer surface 46 comprises the outermost peripheral surface of the bearing 22. The shield 32 forms an annulus volume adjacent the outer race 38 in which lubricant or grease G is packed. The seals 34 cooperate with the shield 32 to minimize leakage of the lubricant G and to provide a barrier to external environmental contamination.

Figure 5:
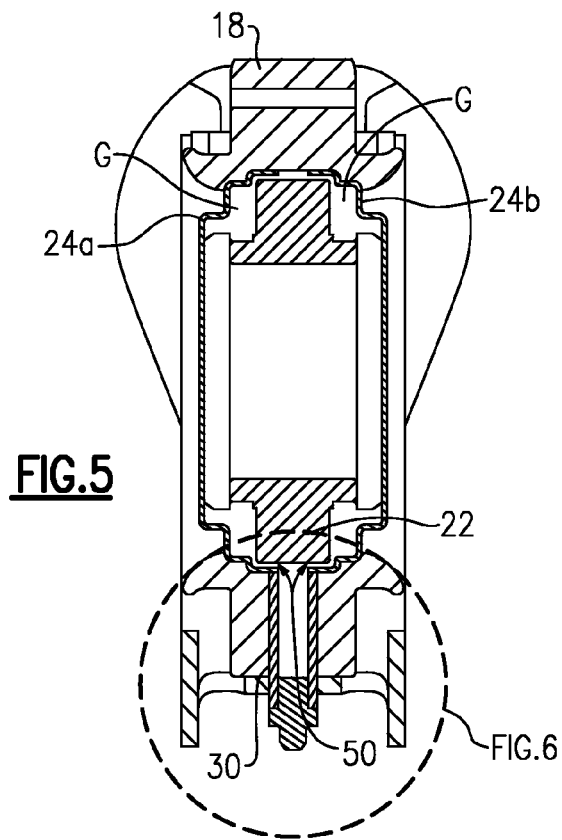
FIG. 5 is a section view taken along lines 5-5 of FIG. 3.
Figure 6:
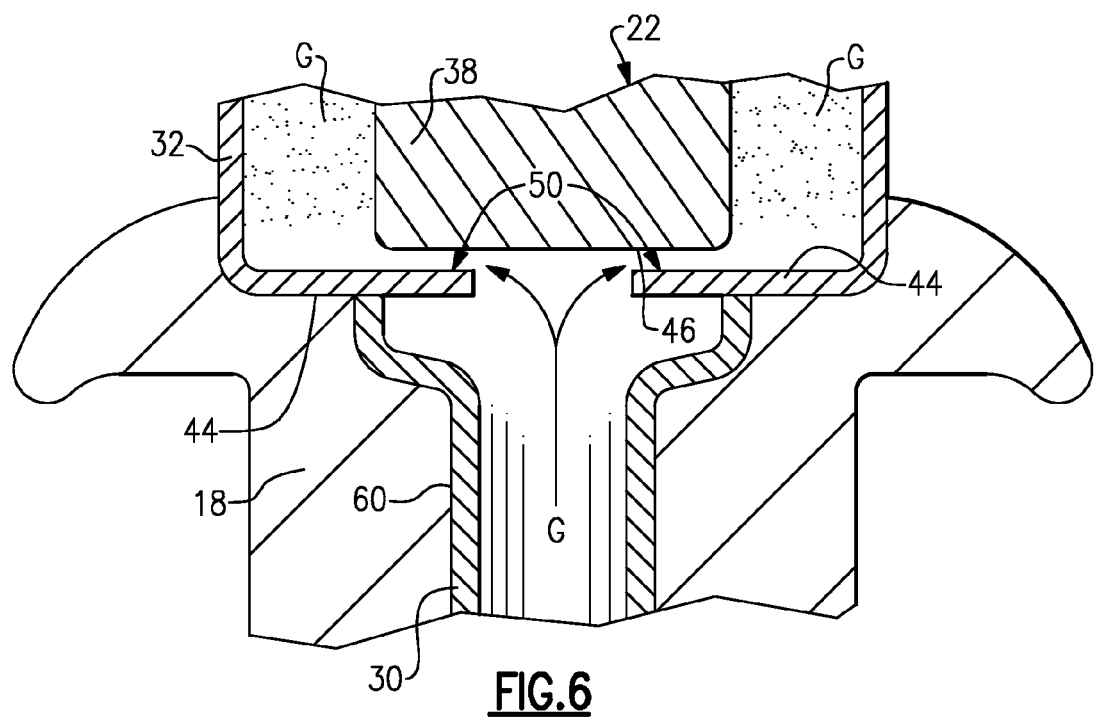
FIG. 6 is a magnified view of corresponding section as indicated in FIG. 5.

As shown in FIGS. 5 and 6, the fitting 30 serves as a mechanism that can replenish the barrier lubricant G to further prevent contaminants from penetrating into the bearing 22. A lubrication (lube) passage 50 is formed between the shield 32 and the outer race 38 of the bearing 22. The lubrication passage 50 includes a first passage that is between the shield 32 of the fore side of the bearing 22 and the outer race 38 and a second passage that is between the shield 32 of the aft side of the bearing 22 and the outer race 38. The fitting 30 is positioned to supply lubricant to both the first and second passages. In the example shown, the fitting 30 is positioned generally centrally between the fore 24a and aft 24b protective assemblies such that lubricant can be easily and efficiently supplied to the lubrication passages extending to both the fore and aft sides of the bearing 22. However, the fitting 30 could be located in other locations, which will be discussed in greater detail below.

When needed, such as during a service or maintenance operation, lubricant is supplied to the bearing 22 via the fitting 30. The lubricant replenishes any grease G that has been depleted from the annulus volume near the outer race 38 as well as re-supplying lubricant to the bearing elements themselves. The seals 34 and shields 32 are configured such that during service, any contaminated lubricant can be pumped out of the bearing 22 with a fresh supply of lubricant replacing the pumped out lubricant.

Figure 7:
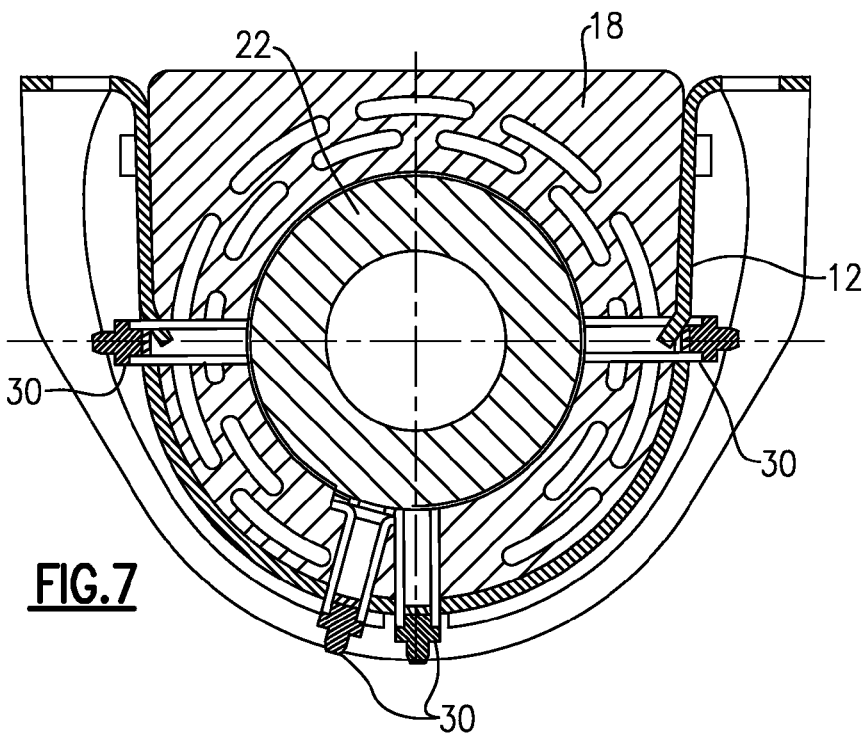
FIG. 7 is a front cross-sectional view of another example of a center support assembly.

In the example shown in FIGS. 2-6, the fitting includes a body 60 that extends through both the resilient cushion 18 and the bracket 12. Thus, the fitting 30 is embedded within the cushion 18. FIG. 7 shows alternate locations of the fitting 30. Further, more than one fitting 30 can be used to supply lubricant to the bearing 22. An example of multiple fittings could include any of the various locations shown in FIG. 7.

Figure 8:
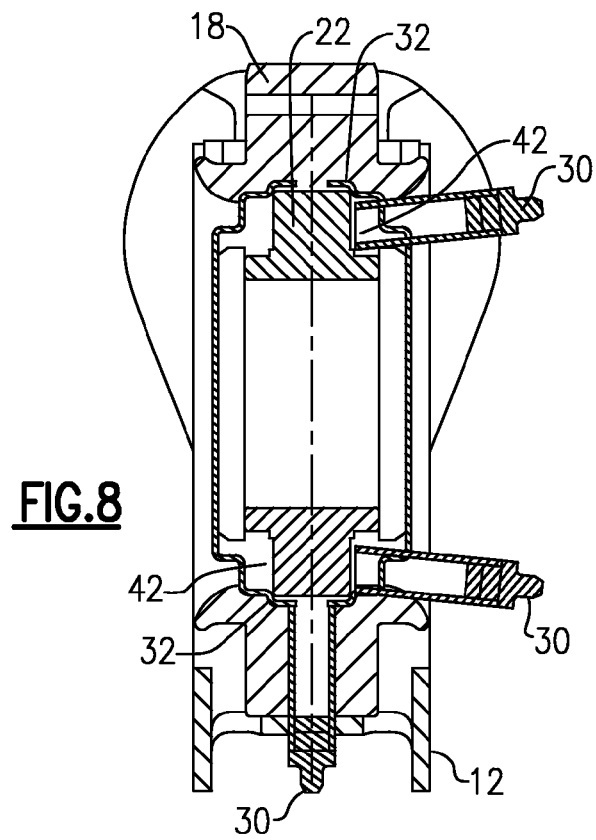
FIG. 8 is a side cross-section view of another example of a center support assembly.

FIG. 8 shows an example where the fitting only extends through the shield 32. The fitting 30 can extend through the first portion 42 of the shield 32 on the fore or aft side of the bearing. Further, multiple fittings 30 could be used on each of the fore and aft sides, or on both of the fore and aft sides. Also, fittings 30 on one bearing 22 could include a fitting that extends through both the cushion and bracket in combination with a fitting that extends only through the shield.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A center support assembly for a driveshaft comprising:
 a bearing to support the driveshaft for rotation about an axis, wherein said bearing has a fore side and an aft side;
 a resilient cushion surrounding said bearing;
 a shield mounted to said bearing, wherein said shield comprises a first shield member and a second shield member with said first shield member being attached to said bearing at said fore side and said second shield member being attached to said bearing at said aft side;
 a seal positioned between said shield and said bearing;
 a lube passage formed between an inner surface of said shield and an outer surface of said bearing; and
 at least one fitting in fluid communication with said lube passage and externally accessible to supply lubricant to said bearing, wherein said fitting includes a body that is embedded within said resilient cushion, said body being in fluid communication with said lube passage.

2. The center support assembly according to claim 1 wherein said at least one fitting extends through said resilient cushion.

3. The center support assembly according to claim 1 wherein said resilient cushion is supported within a bracket adapted for attachment to a vehicle structure.

4. The center support assembly according to claim 3 wherein said at least one fitting extends through said bracket and said resilient cushion.

5. The center support assembly according to claim 1 wherein said shield includes a first portion that extends radially inwardly toward said axis and a second portion that extends over an outer peripheral surface of said bearing, and wherein said lube passage is formed between said outer peripheral surface and an inner surface of said second portion.

6. The center support assembly according to claim 5 wherein said seal is associated with said first portion of said shield.

7. The center support assembly according to claim 6 wherein said seal maintains sealing contact with both said shield and said bearing.

8. The center support assembly according to claim 1 wherein each of said first shield member and said second shield member includes a shield portion that is fixed to an outermost surface of said bearing, and wherein said lube passage includes a fore passage between said shield portion of said first shield member and said outermost surface of said bearing at said fore side and an aft passage between said shield portion of said second shield member and said outermost surface of said bearing at said aft side.

9. The center support assembly according to claim 8 wherein said at least one fitting extends radially inwardly toward said axis at a location that is between said fore passage and said aft passage.

10. The center support assembly according to claim 1 wherein said at least one fitting comprises a plurality of fittings in fluid communication with said lube passage.

11. The center support assembly according to claim 1 wherein the lube passage has a first passage between the first shield member and the fore side of the bearing and a second passage between the second shield member and the aft side of the bearing, and directing lubricant against an outer peripheral surface of the bearing to further direct the lubricant into said first passage and said second passage.

12. The center support assembly according to claim 11 wherein the fitting is positioned generally centrally between the first shield member and the second shield member.

13. The center support assembly according to claim 1 including forming a lube inlet to the lube passage between the first shield member and the second shield member, and wherein the fitting is positioned to be in direct fluid communication with the lube inlet.

14. A method of lubricating a self-aligning center bearing comprising:
  (a) forming a lube passage between an outer surface of the self-aligning center bearing and a shield attached to the self-aligning center bearing, wherein the shield comprises a first shield member and a second shield member with the first shield member being attached to a fore side of the self-aligning center bearing and the second shield member being attached to an aft side of the self-aligning center bearing;
  (b) surrounding the self-aligning center bearing with a resilient cushion; and
  (c) supplying lubricant via at least one external accessible fitting to the lube passage, wherein the at least one external accessible fitting includes a body that is embedded within the resilient cushion, with the body being in fluid communication with the lube passage.

15. The method of lubricating a self-aligning center bearing according to claim 14 wherein the lube passage has a first passage between the first shield member and the fore side of the self-aligning center bearing and a second passage between the second shield member and the aft side of the self-aligning center bearing, and directing lubricant against an outer peripheral surface of the self-aligning center bearing to further direct the lubricant into said first passage and said second passage.

16. The method of lubricating a self-aligning center bearing according to claim 15 wherein the fitting is positioned generally centrally between the first shield member and the second shield member.

17. The method of lubricating a self-aligning center bearing according to claim 14 including forming a lube inlet to the lube passage between the first shield member and the second shield member, and installing the fitting to be in direct fluid communication with the lube inlet.

* * * * *